US012440252B2

(12) United States Patent
Garcia et al.

(10) Patent No.: US 12,440,252 B2
(45) Date of Patent: Oct. 14, 2025

(54) SURGICAL PLATE FASTENER CARTRIDGE

(71) Applicant: Zimmer Biomet CMF and Thoracic, LLC, Jacksonville, FL (US)

(72) Inventors: Saddy Rodolfo Garcia, St. Augustine, FL (US); Jose Ramos, Jersey City, NJ (US); Kevin Lee Teston, Jacksonville, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 315 days.

(21) Appl. No.: 18/120,685

(22) Filed: Mar. 13, 2023

(65) Prior Publication Data

US 2023/0301693 A1 Sep. 28, 2023

Related U.S. Application Data

(60) Provisional application No. 63/324,530, filed on Mar. 28, 2022.

(51) Int. Cl.
*A61B 17/80* (2006.01)

(52) U.S. Cl.
CPC ...... *A61B 17/8047* (2013.01); *A61B 17/8076* (2013.01)

(58) Field of Classification Search
CPC ............ A61B 17/8047; A61B 17/8076; A61B 17/808
See application file for complete search history.

(56) References Cited

U.S. PATENT DOCUMENTS

| | | | |
|---|---|---|---|
| 571,040 | A | 11/1896 | De Vilbiss |
| 1,037,864 | A | 9/1912 | Carlson et al. |
| 1,962,964 | A | 6/1934 | Morrison |
| 2,151,555 | A | 3/1939 | Kimball |
| 2,226,393 | A | 12/1940 | Seeger et al. |
| 2,443,335 | A | 6/1948 | Louis |

(Continued)

FOREIGN PATENT DOCUMENTS

| | | | |
|---|---|---|---|
| CN | 101040796 | A | 9/2007 |
| CN | 201085676 | Y | 7/2008 |

(Continued)

OTHER PUBLICATIONS

U.S. Appl. No. 14/466,485 U.S. Pat. No. 10,010,359, filed Aug. 22, 2014, Sternal Closure Cerclage, Plate Implant and Instrumentation.

(Continued)

*Primary Examiner* — Si Ming Ku
(74) *Attorney, Agent, or Firm* — SCHWEGMAN LUNDBERG & WOESSNER, P.A.

(57) ABSTRACT

A fastener cartridge can include a body defining a plurality of retention bores that can each extend through the body and can each be configured to retain a fastener therein. The cartridge can also include a boss, a cam, and an actuator. The boss can extend from the body and can be insertable into a connection bore of a bone plate to align each retention bore with a fastener bore of the bone plate. The cam can be connected to the body and can be rotatable between a locked position and an unlocked position. The cam can be operated by the actuator and can be engageable with a body of the plate in the locked position to secure the plate to the cartridge.

19 Claims, 10 Drawing Sheets

(56) References Cited

U.S. PATENT DOCUMENTS

| | | | |
|---|---|---|---|
| 3,045,306 | A | 7/1962 | Taylor |
| 3,111,945 | A | 11/1963 | Von Solbrig |
| 4,371,192 | A | 2/1983 | Alix |
| 5,070,805 | A | 12/1991 | Plante |
| 5,139,498 | A | 8/1992 | Astudillo Ley |
| 5,190,545 | A | 3/1993 | Corsi et al. |
| 5,335,400 | A | 8/1994 | Sales |
| 5,356,412 | A | 10/1994 | Golds et al. |
| 5,383,905 | A | 1/1995 | Golds et al. |
| 5,415,658 | A | 5/1995 | Kilpela et al. |
| 5,423,821 | A | 6/1995 | Pasque |
| 5,772,663 | A | 6/1998 | Whiteside et al. |
| 6,015,428 | A | 1/2000 | Pagedas |
| 6,017,347 | A | 1/2000 | Huebner et al. |
| 6,030,410 | A | 2/2000 | Zurbrugg |
| 6,066,160 | A | 5/2000 | Colvin et al. |
| 6,120,505 | A | 9/2000 | Huebner |
| 6,302,889 | B1 | 10/2001 | Keller |
| 6,682,533 | B1 | 1/2004 | Dinsdale et al. |
| 6,712,821 | B2 | 3/2004 | Gabbay |
| 6,974,452 | B1 | 12/2005 | Gille et al. |
| 7,052,499 | B2 | 5/2006 | Steger et al. |
| 7,458,981 | B2 | 12/2008 | Fielding et al. |
| 7,803,176 | B2 | 9/2010 | Teague et al. |
| 8,172,887 | B2 | 5/2012 | Gabele |
| 8,414,594 | B2 | 4/2013 | Berger et al. |
| 8,652,137 | B2 | 2/2014 | Blain et al. |
| 8,679,122 | B2 | 3/2014 | Bernstein et al. |
| 8,992,533 | B2 | 3/2015 | Blain et al. |
| 9,060,787 | B2 | 6/2015 | Blain et al. |
| 9,295,507 | B2 | 3/2016 | Albertson et al. |
| 9,358,054 | B2 | 6/2016 | Garcia et al. |
| 9,788,878 | B2 | 10/2017 | Garcia et al. |
| 9,801,672 | B2 | 10/2017 | Garcia et al. |
| 9,820,755 | B2 | 11/2017 | Garcia et al. |
| 10,010,359 | B2 | 7/2018 | Garcia et al. |
| 10,307,193 | B2 | 6/2019 | Garcia et al. |
| 10,639,084 | B2 | 5/2020 | Garcia et al. |
| 10,939,927 | B2 | 3/2021 | Garcia et al. |
| 10,952,756 | B2 | 3/2021 | Garcia et al. |
| 11,678,895 | B2 | 6/2023 | Garcia et al. |
| 2003/0083669 | A1 | 5/2003 | Gleason |
| 2004/0034352 | A1 | 2/2004 | Needham et al. |
| 2005/0240191 | A1 | 10/2005 | Albertson et al. |
| 2006/0111721 | A1 | 5/2006 | Puricelli |
| 2006/0195104 | A1 | 8/2006 | Schlafli et al. |
| 2007/0260251 | A1 | 11/2007 | Weier et al. |
| 2008/0140128 | A1 | 6/2008 | Smisson et al. |
| 2010/0094294 | A1 | 4/2010 | Gillard et al. |
| 2010/0179600 | A1 | 7/2010 | Steger et al. |
| 2011/0028979 | A1 | 2/2011 | Schwab |
| 2011/0035008 | A1 | 2/2011 | Williams |
| 2012/0059377 | A1 | 3/2012 | Belliard |
| 2012/0130373 | A1 | 5/2012 | Larroque-Lahitette |
| 2012/0157998 | A1 | 6/2012 | Belliard |
| 2012/0215224 | A1 | 8/2012 | Songer |
| 2012/0290017 | A1 | 11/2012 | Haidukewych |
| 2012/0303065 | A1 | 11/2012 | Larroque-Lahitette et al. |
| 2013/0178854 | A1 | 7/2013 | Sholev |
| 2013/0261625 | A1 | 10/2013 | Koch et al. |
| 2015/0038969 | A1 | 2/2015 | Garcia et al. |
| 2015/0045794 | A1 | 2/2015 | Garcia et al. |
| 2015/0342657 | A1 | 12/2015 | Voisard et al. |
| 2016/0051297 | A1 | 2/2016 | Steffensmeier et al. |
| 2016/0296262 | A1 | 10/2016 | Garcia et al. |
| 2016/0317161 | A1 | 11/2016 | Garcia |
| 2016/0331431 | A1 | 11/2016 | Gephart |
| 2017/0086894 | A1 | 3/2017 | Garcia et al. |
| 2018/0132864 | A1 | 5/2018 | Garcia et al. |
| 2019/0269447 | A1 | 9/2019 | Garcia et al. |
| 2019/0380756 | A1 | 12/2019 | Garcia et al. |
| 2020/0078063 | A1 | 3/2020 | Garcia et al. |
| 2020/0337751 | A1* | 10/2020 | Detweiler .......... A61B 17/8038 |
| 2021/0259717 | A1 | 8/2021 | Garcia et al. |

FOREIGN PATENT DOCUMENTS

| | | | |
|---|---|---|---|
| CN | 101938948 | A | 1/2011 |
| CN | 202235652 | U | 5/2012 |
| CN | 202604988 | U | 12/2012 |
| CN | 202612933 | U | 12/2012 |
| CN | 103099665 | A | 5/2013 |
| CN | 106413608 | A | 2/2017 |
| CN | 111772757 | A | 10/2020 |
| DE | 3427590 | A1 | 2/1986 |
| DE | 3538645 | A1 | 5/1987 |
| DE | 4021246 | A1 | 1/1992 |
| DE | 19527151 | A1 | 1/1997 |
| EP | 876798 | A2 | 11/1998 |
| EP | 3116424 | A2 | 1/2017 |
| EP | 3498207 | A1 | 6/2019 |
| JP | 2002511281 | A | 4/2002 |
| JP | 3106821 | B2 | 11/2004 |
| JP | 2017507758 | A | 3/2017 |
| JP | 2019217349 | A | 12/2019 |
| WO | WO-9522294 | A1 | 8/1995 |
| WO | WO-03037196 | A1 | 5/2003 |
| WO | WO-2003037196 | A1 | 5/2003 |
| WO | WO-2007056399 | A1 | 5/2007 |
| WO | WO-2009100339 | A1 | 8/2009 |
| WO | WO-2013003719 | A1 | 1/2013 |
| WO | WO-2014144479 | A1 | 9/2014 |
| WO | WO-2015142588 | A2 | 9/2015 |
| WO | WO-2015142588 | A3 | 9/2015 |

OTHER PUBLICATIONS

U.S. Appl. No. 14/500,010 U.S. Pat. No. 9,358,054, filed Sep. 29, 2014, Sternal Closure Cerclage, Plate Implant and Instrumentation.

U.S. Appl. No. 15/174,041 U.S. Pat. No. 9,788,878, filed Jun. 6, 2016, Sternal Closure Cerclage, Plate Implant and Instrumentation.

U.S. Appl. No. 15/174,783 U.S. Pat. No. 9,801,672, filed Jun. 6, 2016, Sternal Closure Cerclage, Plate Implant and Instrumentation.

U.S. Appl. No. 15/204,515 U.S. Pat. No. 9,820,755, filed Jul. 7, 2016, Sternal Closure Cerclage, Plate Implant and Instrumentation.

U.S. Appl. No. 15/815,783 U.S. Pat. No. 10,307,193, filed Nov. 17, 2017, Sternal Closure Cerclage, Plate Implant and Instrumentation.

U.S. Appl. No. 16/418,217 U.S. Pat. No. 10,952,756, filed May 21, 2019, Sternal Closure System.

U.S. Appl. No. 16/421,762 U.S. Pat. No. 10,939,927, filed May 24, 2019, Sternal Closure Method.

U.S. Appl. No. 16/682,775 U.S. Pat. No. 10,639,084, filed Nov. 13, 2019, Sternal Closure Method and System.

U.S. Appl. No. 17/171,882, filed Feb. 9, 2021, Sternal Closure System.

"U.S. Appl. No. 14/466,485, Non Final Office Action mailed Oct. 27, 2017", 9 pgs.

"U.S. Appl. No. 14/466,485, Notice of Allowance mailed Mar. 5, 2018", 8 pgs.

"U.S. Appl. No. 14/466,485, Response filed Jan. 29, 2018 to Non Final Office Action mailed Oct. 27, 2017", 11 pgs.

"U.S. Appl. No. 14/466,485, Response filed Jul. 24, 2017 to Restriction Requirement mailed May 23, 2017", 10 pgs.

"U.S. Appl. No. 14/466,485, Restriction Requirement mailed May 23, 2017", 7 pgs.

"U.S. Appl. No. 14/500,010, Final Office Action mailed Oct. 26, 2015", 6 pgs.

"U.S. Appl. No. 14/500,010, Non Final Office Action mailed Jun. 9, 2015", 7 pgs.

"U.S. Appl. No. 14/500,010, Notice of Allowance mailed Feb. 5, 2016", 6 pgs.

"U.S. Appl. No. 14/500,010, Response filed Jan. 26, 2016 to Final Office Action mailed Oct. 26, 2015", 9 pgs.

"U.S. Appl. No. 14/500,010, Response filed May 29, 2015 to Restriction Requirement mailed Mar. 5, 2015", 11 pgs.

"U.S. Appl. No. 14/500,010, Response filed Oct. 9, 2015 to Non Final Office Action mailed Jun. 9, 2015", 13 pgs.

"U.S. Appl. No. 14/500,010, Restriction Requirement mailed Mar. 5, 2015", 8 pgs.

(56) References Cited

OTHER PUBLICATIONS

"U.S. Appl. No. 15/174,041, Notice of Allowance mailed Jun. 14, 2017", 7 pgs.
"U.S. Appl. No. 15/174,041, Preliminary Amendment filed Dec. 20, 2016", 6 pgs.
"U.S. Appl. No. 15/174,783, Notice of Allowance mailed Jun. 28, 2017", 9 pgs.
"U.S. Appl. No. 15/204,515, Notice of Allowance mailed Jul. 14, 2017", 10 pgs.
"U.S. Appl. No. 15/204,515, Preliminary Amendment filed Aug. 31, 2016", 4 pgs.
"U.S. Appl. No. 15/204,515, PTO Response to Rule 312 Communication mailed Oct. 16, 2017", 2 pgs.
"U.S. Appl. No. 15/815,783, Notice of Allowance mailed Mar. 20, 2019", 5 pgs.
"U.S. Appl. No. 15/815,783, Notice of Allowance mailed Dec. 13, 2018", 7 pgs.
"U.S. Appl. No. 15/815,783, Preliminary Amendment filed Feb. 7, 2018", 5 pgs.
"U.S. Appl. No. 15/815,783, Response filed Feb. 22, 2019", 8 pgs.
"U.S. Appl. No. 16/418,217, Notice of Allowability mailed Jan. 27, 2021", 4 pgs.
"U.S. Appl. No. 16/418,217, Notice of Allowance mailed Nov. 13, 2020", 8 pgs.
"U.S. Appl. No. 16/418,217, Preliminary Amendment filed Nov. 13, 2019", 7 pgs.
"U.S. Appl. No. 16/421,762, Notice of Allowability mailed Jan. 27, 2021", 4 pgs.
"U.S. Appl. No. 16/421,762, Notice of Allowance mailed Nov. 4, 2020", 8 pgs.
"U.S. Appl. No. 16/421,762, Preliminary Amendment filed Nov. 13, 2019", 7 pgs.
"U.S. Appl. No. 16/682,775, Notice of Allowance mailed Jan. 30, 2020", 7 pgs.
"U.S. Appl. No. 17/171,882, Notice of Allowance mailed Jan. 25, 2023", 9 pgs.
"U.S. Appl. No. 17/171,882, Preliminary Amendment filed May 25, 2021", 7 pgs.
"U.S. Appl. No. 17/171,882, PTO Response to Rule 312 Communication mailed Mar. 2, 2023", 2 pgs.
"Australian Application Serial No. 2015231821, First Examination Report mailed Dec. 4, 2018", 4 pgs.
"Australian Application Serial No. 2020201496, First Examination Report mailed Sep. 3, 2020", 4 pgs.
"Australian Application Serial No. 2021254673, Amendment Filed Apr. 5, 2022", 52 pgs.
"Canadian Application Serial No. 2,942,854, Office Action mailed Apr. 2, 2020", 4 pgs.
"Canadian Application Serial No. 2,942,854, Response filed Jul. 28, 2020 to Office Action mailed Apr. 2, 2020", 14 pgs.
"Chinese Application Serial No. 201580023355.5, Office Action mailed Jan. 3, 2020", (w/ English Translation), 16 pgs.
"Chinese Application Serial No. 201580023355.5, Office Action mailed Mar. 25, 2020", (w/ English Translation), 7 pgs.
"Chinese Application Serial No. 201580023355.5, Office Action mailed Apr. 2, 2019", w/ English Translation, 12 pgs.
"Chinese Application Serial No. 201580023355.5, Office Action mailed Jun. 4, 2018", w/ English translation, 10 pgs.
"Chinese Application Serial No. 201580023355.5, Response filed Apr. 28, 2020 to Office Action mailed Mar. 25, 2020", (w/ English Translation of Claims), 13 pgs.
"Chinese Application Serial No. 201580023355.5, Response filed Aug. 16, 2019 to Office Action mailed Apr. 2, 2019", w/ English claims, 14 pgs.
"Chinese Application Serial No. 201580023355.5, Response filed Oct. 17, 2018 to Office Action mailed Jun. 4, 2018", (W/ English Claims), 14 pgs.
"Chinese Application Serial No. 201580023355.5, Response filed Office Action mailed Jan. 3, 2020", (W/ English Translation of Claims), 19 pgs.
"Chinese Application Serial No. 202010770615.8, Decision of Rejection mailed Jan. 5, 2023", w/ English Translation, 11 pgs.
"Chinese Application Serial No. 202010770615.8, Office Action mailed Jun. 2, 2022", w/ English translation, 11 pgs.
"Chinese Application Serial No. 202010770615.8, Office Action mailed Nov. 18, 2021", W/English Translation, 16 pgs.
"Chinese Application Serial No. 202010770615.8, Response filed Feb. 21, 2022 to Office Action mailed Nov. 18, 2021", w/ English claims, 10 pgs.
"Chinese Application Serial No. 202010770615.8, Response filed Aug. 1, 2022 to Office Action mailed Jun. 2, 2022", w/ English claims, 12 pgs.
"English translation of EP 876798", (Jun. 3, 2015), 6 pgs.
"European Application Serial No. 14716195.4, Response filed May 16, 2016 to Communication pursuant to Rules 161(1) and 162 EPC mailed Nov. 5, 2015", 10 pgs.
"European Application Serial No. 15734485.4, Response filed Jun. 2, 2017 to Communication pursuant to Rules 161(1) and 162 EPC mailed Nov. 22, 2016", 16 pgs.
"European Application Serial No. 18171347.0, Communication Pursuant to Article 94(3) EPC mailed Sep. 27, 2022", 6 pgs.
"European Application Serial No. 18171347.0, Extended European Search Report mailed May 21, 2019", 7 pgs.
"European Application Serial No. 18171347.0, Response filed Feb. 7, 2023 to Communication Pursuant to Article 94(3) EPC mailed Sep. 27, 2022", 11 pgs.
"European Application Serial No. 18171347.0, Response filed Dec. 19, 2019 to Extended European Search Report mailed May 21, 2019", 8 pgs.
"European Application Serial No. 19179523.6, Extended European Search Report mailed Oct. 29, 2019", 7 pgs.
"European Serial No. 14716195.4, Response filed Jul. 24, 2017 to Office Action Mailed Mar. 13, 2017", 16 pgs.
"International Application Serial No. PCT/US2012/044920, International Search Report mailed Sep. 25, 2012", 3 pgs.
"International Application Serial No. PCT/US2012/044920, Written Opinion mailed Sep. 25, 2012", 8 pgs.
"International Application Serial No. PCT/US2014/028903, International Preliminary Report on Patentability mailed Sep. 24, 2015", 7 pgs.
"International Application Serial No. PCT/US2014/028903, International Search Report mailed Jun. 30, 2014", 3 pgs.
"International Application Serial No. PCT/US2014/028903, Written Opinion mailed Jun. 30, 2014".
"International Application Serial No. PCT/US2015/019976, International Preliminary Report on Patentability mailed Sep. 22, 2016", 12 pgs.
"International Application Serial No. PCT/US2015/019976, International Search Report mailed Nov. 17, 2015", 7 pgs.
"International Application Serial No. PCT/US2015/019976, Invitation to Pay Additional Fees and Partial Search Report mailed Sep. 7, 2015", 6 pgs.
"International Application Serial No. PCT/US2015/019976, Written Opinion mailed Nov. 17, 2015", 10 pgs.
"Japanese Application Serial No. 2016-557940, Office Action mailed Nov. 20, 2018", w/ English translation, 5 pgs.
"Japanese Application Serial No. 2016-557940, Response filed May 17, 2019 to Office Action mailed Nov. 20, 2018", w/ English claims, 13 pgs.
"Japanese Application Serial No. 2019-160521, Notification of Reasons for Refusal mailed Nov. 17, 2020", with English translation, 5 pgs.
"Locking Mechanism to Secure the Ends of an Implantable Braid", Patentability Search Report, (Feb. 5, 2011), 3 pgs.
"European Application Serial No. 18171347.0, Communication Pursuant to Article 94(3) EPC mailed Jun. 27, 2024", 5 pgs.
"European Application Serial No. 18171347.0, Response filed Oct. 11, 2024 to Communication Pursuant to Article 94(3) EPC mailed Jun. 27, 2024", 7 pgs.
"European Application Serial No. 18171347.0, Summons to Attend Oral Proceedings mailed Feb. 6, 2025", 5 pgs.

* cited by examiner

SURGICAL PLATE FASTENER CARTRIDGE

CLAIM OF PRIORITY

This application claims the benefit of U.S. Provisional Patent Application Ser. No. 63/324,530, filed on Mar. 28, 2022, the benefit of priority of which is claimed hereby, and which is incorporated by reference herein in its entirety.

BACKGROUND

A sternotomy is a procedure performed to separate a sternum of a patient to gain access to the chest cavity of the patient, such as for corrective heart procedures. During a sternotomy procedure a vertical (superior to inferior) cut is made through the sternum allowing the sternum to be cracked or separated into two or more portions to provide access to the chest cavity. Following a procedure within the chest cavity, the sternum must be closed. Commonly, sternotomies are closed or repaired using one or more wire cerclages wrapped around the sternal halves. In some cases, at least one rigid bone plate is used to bridge and secure to the approximated and reduced sternal halves using bone screws.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Sternotomies are often performed on a sternum of a patient (such as prior to a cardiac procedure) by creating a midline resection and separating two halves or portions of the sternum for access to the chest cavity of the patient. Following the procedure, the sternum is often repaired using one or more wire cerclages to hold the sternal halves in place while the halves heal together. While wire cerclages can help to prevent medial-lateral separation (or relative movement of the halves) of the sternum, wire cerclages are sometimes ineffective at limiting relative anterior-posterior movement of the halves and at limiting relative superior-inferior movement of the halves. Wire cerclages can also unintentionally penetrate outer portions of the sternum. Rigid bone plates are a strategy often used to address the shortcomings of wire cerclages. Rigid bone plates can be secured to each portion or half of the sternum and can help to limit relative movement of the sternal halves in all directions. Nevertheless, it can be difficult to position and secure the bone plates following reduction of the sternal halves.

This disclosure helps to address these issues by including a fastener cartridge configured to support fasteners and the bone plate for positioning of the bone plate and fasteners on the sternal portions. The cartridge can be configured to support and retain fasteners therein for alignment with bores of the bone plate and can hold the bone plate while fasteners are driven out of the cartridge, through the bone plate, and into bone. In this way, the plate system can help to provide reliable fastener driving during securing of the bone plate. Additionally, the cartridge can be configured to quickly receive and retain fasteners therein to help improve speed of a procedure. Further, the cartridge can be releasably connectable to a placement tool for improved ergonomics and leverage during securing of the plate. Also, the cartridge can include a lock to releasably secure the plate to the cartridge for additional security during fastening of the plate to bone.

The above discussion is intended to provide an overview of the subject matter of the present patent application. It is not intended to provide an exclusive or exhaustive explanation of the invention. The description below is included to provide further information about the present patent application.

Figure 1B:
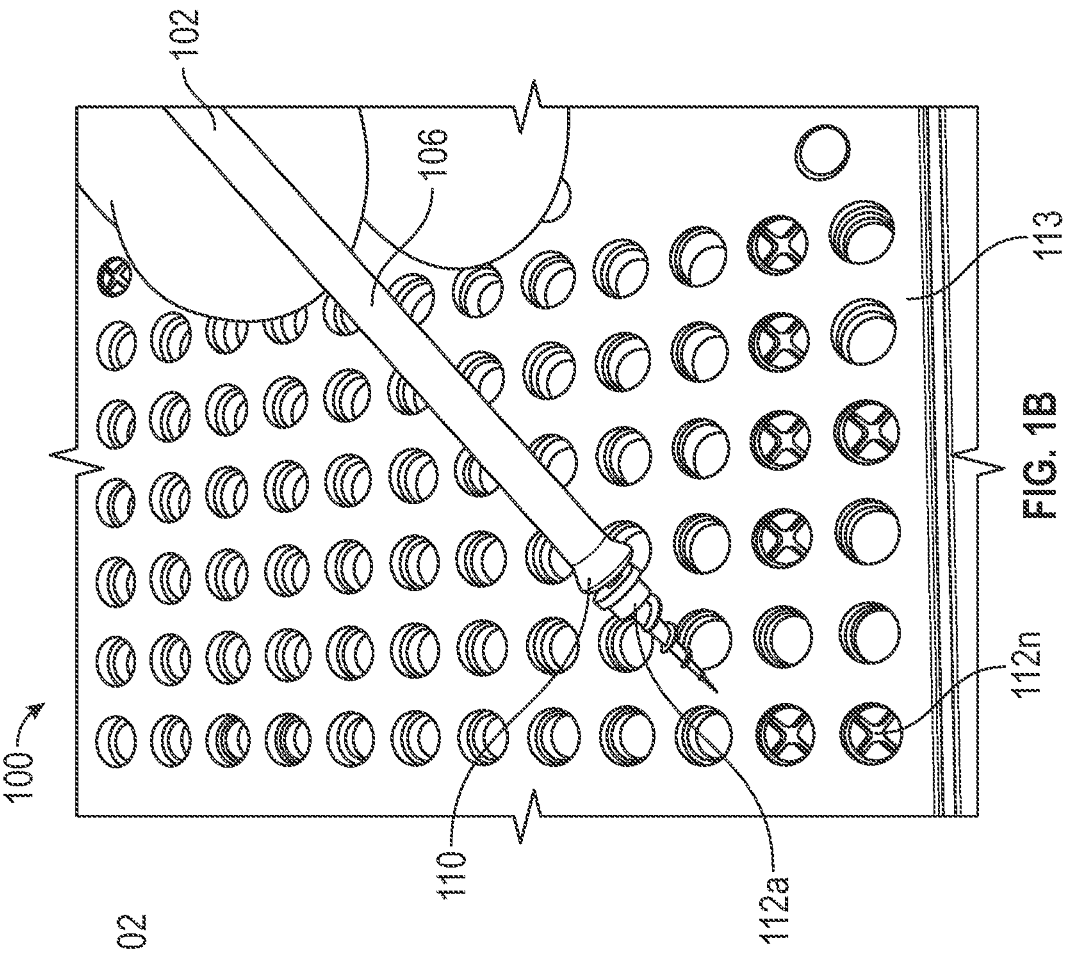
FIG. 1B illustrates a perspective view of a portion of a plating system.
Figure 1A:
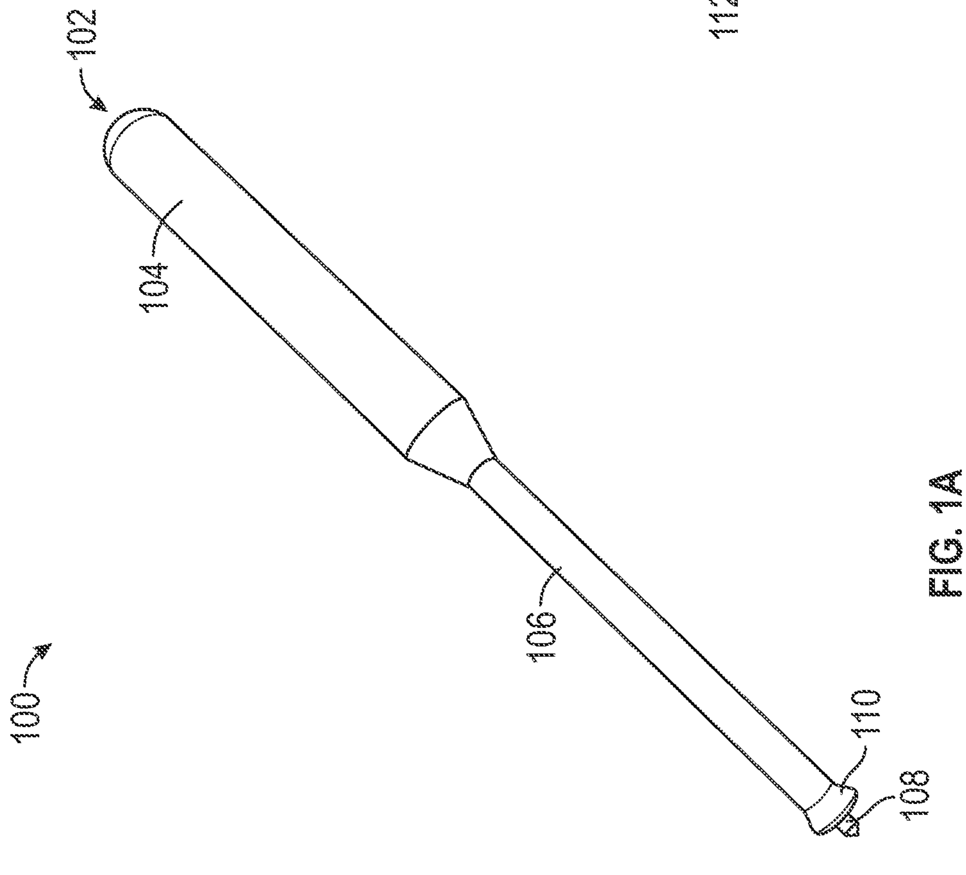
FIG. 1A illustrates a perspective view of a portion of a plating system.
Figure 1C:
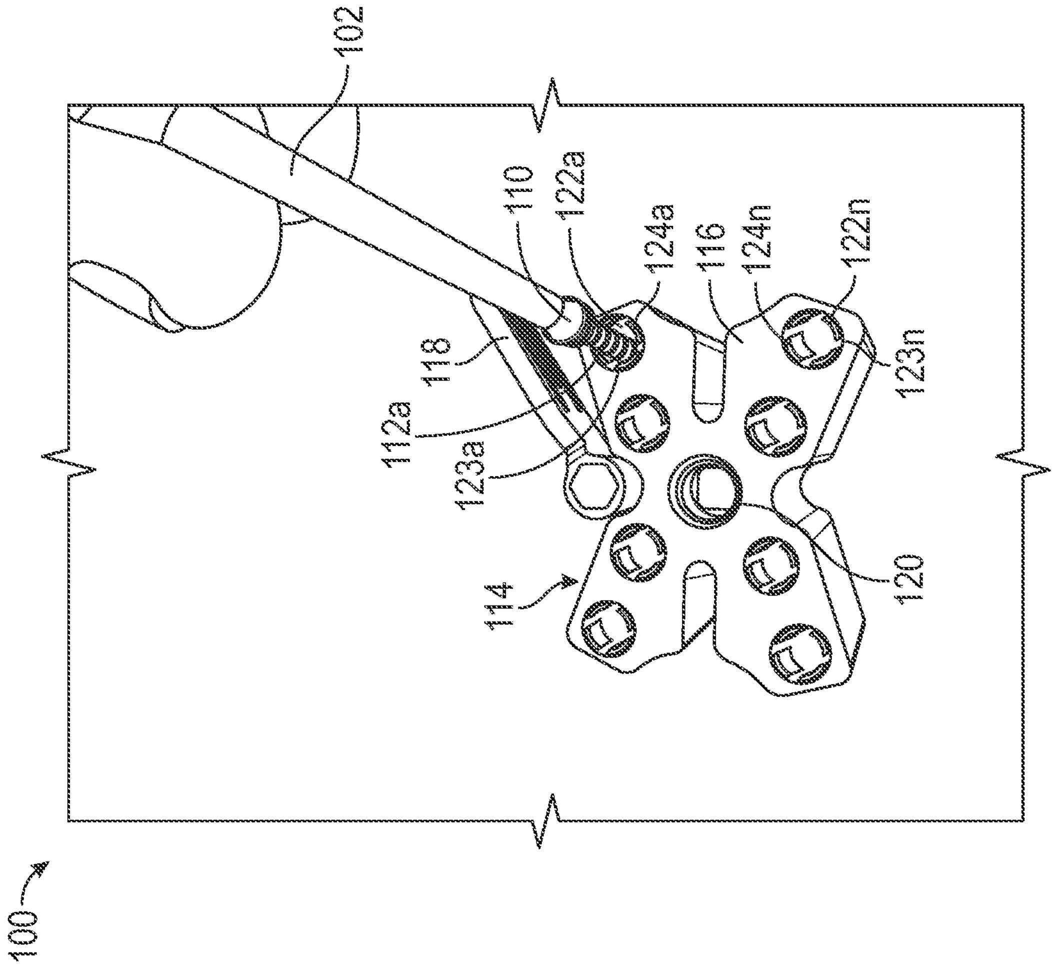
FIG. 1C illustrates a perspective view of a portion of a plating system.

FIG. 1A illustrates a perspective view of a portion of a plating system 100. FIG. 1B illustrates a perspective view of a portion of the plating system 100. FIG. 1C illustrates a perspective view of a portion of the plating system 100. FIGS. 1A-1C are discussed below. Though only some components of the plating system 100 are discussed with respect to FIGS. 1A-1C, other components discussed further below can be included in the plating system 100.

The plating system 100 can include a wand 102. The wand 102 can include a handle 104, a shaft 106, a tip 108, and a shoulder 110. The plating system 100 can also include fasteners 112*a*-112*n*. As shown in FIG. 1C, the plating system 100 can also include a cartridge 114 including a body 116 and a lock 118. The body 116 can define a placement bore 120 and retention bores 122*a*-122*n*. The cartridge 114 can also include retention sleeves 124*a*-124*n*.

The wand 102 can be a rigid or semi-rigid instrument made of materials such as metals, plastics, foams, elastomers, ceramics, composites, or combinations thereof. In some examples, the wand 102 can be comprised of biocompatible materials such as such as one or more of stainless steels, cobalt-chromium, titanium variations, polyether ether ketone (PEEK), polyether ketone ketone (PEKK), or the like.

The body 116 can be a rigid or semi-rigid body. The body 116 can be made of materials such as metals, plastics, foams, elastomers, ceramics, composites, or combinations thereof. In some examples, the body 116 can be comprised of biocompatible materials such as such as one or more of stainless steels, cobalt-chromium, titanium variations, polyether ether ketone (PEEK), polyether ketone ketone (PEKK), or the like. In one example, the body 116 can be comprised of PEEK and can be coated with titanium and/or a hydroxyapatite coating. The lock 118 can be connected to the body 116 and can be operable to secure a plate to the body 116. The retention bores 122 can be configured to receive and retain fasteners therein, as discussed in further detail with respect to FIG. 2.

As shown in FIG. 1B, the wand 102 can be used to quickly retrieve fasteners (e.g., 112*a*) from a tray 113, allowing the wand 102 to be used to repeatedly place fasteners retrieved from the tray into bores of a screw cartridge. As shown in FIGS. 1B and 1C, the tip 108 can be configured to engage and retain the fasteners 112, such as through an interference or friction interface. Optionally, the tip 108 can be magnetized to retain fasteners thereon. As shown in FIG. 1C, once a fastener (e.g., 112*a*) is retained on the wand 102, the handle 104 can be operated to position the fastener 112*a* into a retaining bore 122*a* of the body 116.

The shoulder 110 can be configured to engage a head of the fasteners 112, such as for applying a force to the fasteners 112, as discussed in further detail below, to force the fastener 112*a* into the bore 122*a*. Optionally, the shoulder 110 can be configured to engage the cartridge 114 to guide insertion of the fasteners 112 into the retention bores 122 at a proper depth or position.

FIG. 1C also show sleeves 124*a*-124*n* of the cartridge 114, which can be retained within bores 123*a*-123*n* of the cartridge, respectively, to define the retention bores 122*a*-122*n*, through the cartridge 114, respectively. The sleeves 124 can be press fit into the bores 123 to retain the sleeves 124 in an interference fit, but the sleeves 124 can be secured in other ways such as via threading or adhesive.

Figure 2:
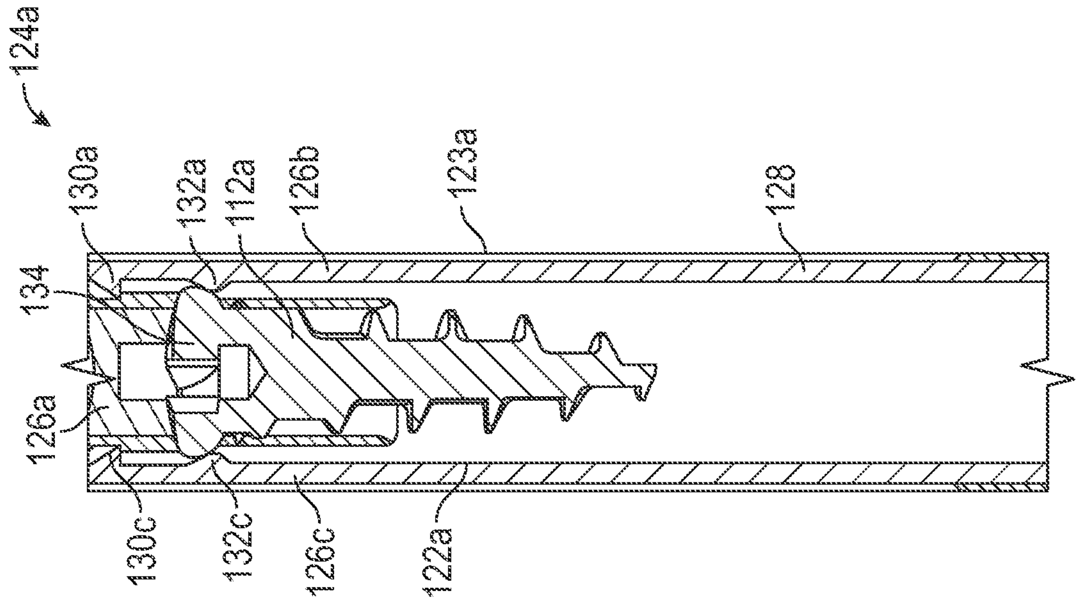
FIG. 2 illustrates a cross-sectional view of a portion of a fastener cartridge.

FIG. 2 illustrates a cross-sectional view of a portion of the fastener cartridge 114. The cartridge 114 can be consistent with FIG. 1C discussed above; FIG. 2 shows additional details of the cartridge 114; for example, FIG. 2 shows the retention sleeve 124*a* retaining the fastener 112*a* in the retention bore 122*a*.

The sleeve 124*a* can be a sleeve or tube insertable into a bore of the body 116 of the cartridge 114. The retention sleeve 124*a* can include extensions 126*a*-126*d* extending from a base portion 128 of the sleeve 124*a*. Though three of the extensions 126 are shown in FIG. 2, FIG. 1C shows that each 124 can include four extensions. Optionally, each sleeve 124 can include more or less extensions, such as 2, 3, 5, 6, 7, 8, 9, 10, or the like. The extensions 126 can be a proximal portion of the sleeve 124*a* cantilevered from the base portion 128 such as to allow the extensions 126 to reversibly deflect radially outward (such as under elastic deflection) such as to allow the fastener 112*a* to be inserted into and be moved out of the retention bore 122*a*. The extensions 126 and the base portion 128 can be spaced from the bore 123*a* to allow for deflection of the extensions 126 within the bore 123*a*.

Each extension 126*a* can include a proximal retention feature 130 and a distal retention feature 132. The retention features 130 and 132 can be projections or extensions from their respective extension configured to extend radially into the retention bore 122*a*. Each proximal retention feature 130 and distal retention feature 132 can include a radially inner diameter forming an opening that is smaller than that of a head 134 of the fastener 112*a*, such that the retention features 130 and 132 can engage the head 134 of the fastener for retention of the fastener within the retention bore 122*a*.

In operation of some examples, when a fastener, such as the fastener 112*a* is secured to the tip 108 of the wand 102, a user can manipulate the handle 104 to position a tip or leading portion of the fastener within the retention bore 122*a* of the sleeve 124*a*, as shown in FIG. 1C. As the fastener 112*a* is inserted into the retention bore 122*a*, the head 134*a* can engage the proximal retention features 130 of the extensions 126. If a proximal to distal force is applied by the user on the fastener 112*a*, the head 134 can engage ramped surfaces of the proximal retention features 130, causing radially outward deflection of the extensions 126, allowing the fastener 112*a* to enter the retention bore 122*a* until the head 134 engages the distal retention features 132, capturing the fastener 112*a* between the proximal retention features 130 and the distal retention features 132.

Because the distal retention feature 132 are closer to the connection point between the extensions 126 and the base portion 128, a force required to cause radially outward deflection of the extensions 126 sufficient for the head 134 to pass is larger for the distal retention features 132 than the proximal retention features 130. In this way, the distal retention features 132 can limit further distal movement of the fastener 112*a* through the retention bore 122*a* unless a user increases the proximal to distal force applied to the fastener 112*a*.

Also, once the head 134 clears the proximal retention features 130, the extensions 126 can deflect back radially inward, capturing the fastener 112*a* between the proximal retention features 130 and the distal retention features 132. Optionally, the proximal retention features 130 can include a distal flat surface (or non-ramped surface) such that proximal movement of the fastener 112*a* to engage the proximal retention features 130 will require a large force to cause radially outward deflection of the extensions 126, helping to retain the fastener 112*a* therein.

When a user desires to drive the fastener 112*a* out of the retention bore 122*a*, the user can apply a proximal to distal force to the head 134 to engage the distal retention features 132 sufficient to cause radially outward deflection of the extensions 126 to expand an opening or passage of the distal retention features 132 to allow movement of the fastener 112*a* into and through the retention bore 122*a* such that the fastener 112*a* can be driven into a plate and a bone, as discussed in further detail below.

Figure 3A:
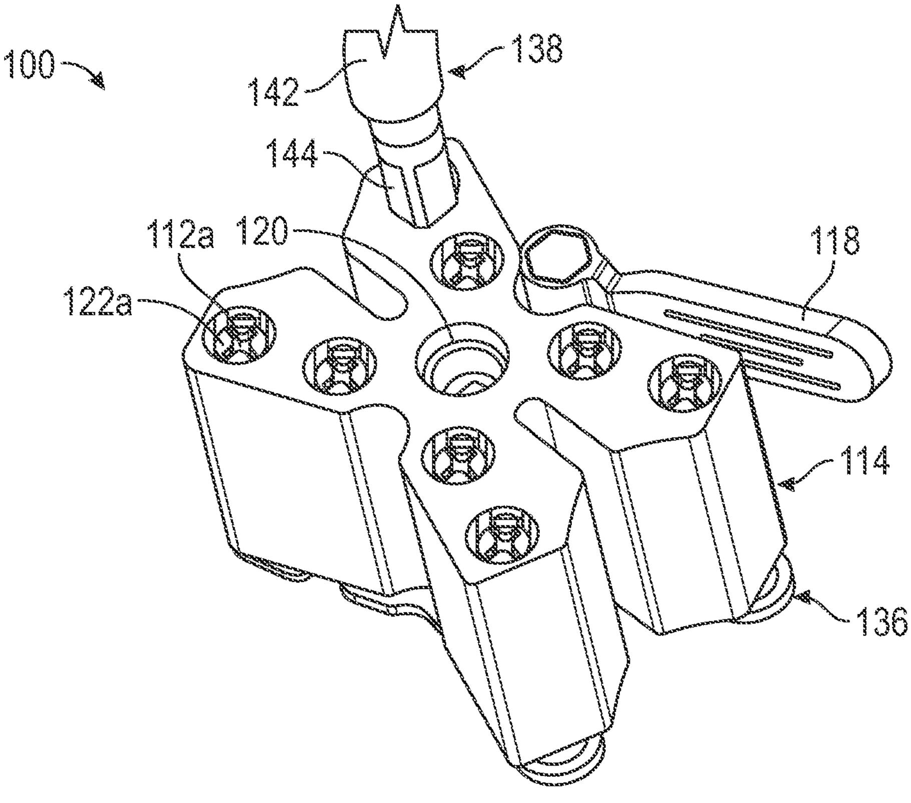
FIG. 3A illustrates a perspective view of a portion of a plating system.
Figure 3B:
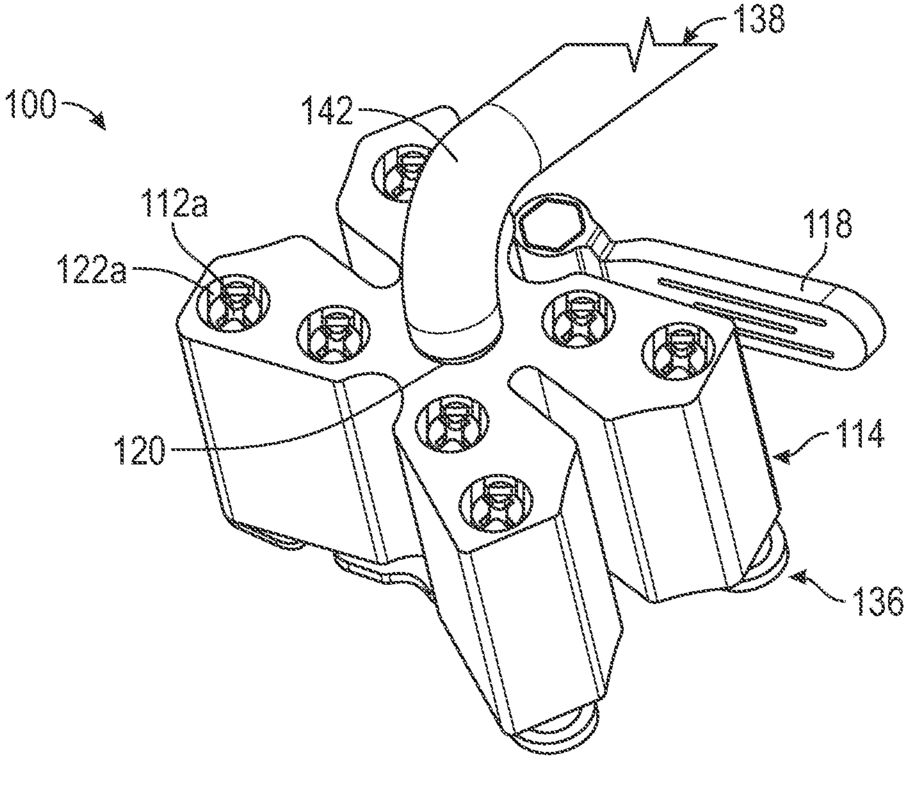
FIG. 3B illustrates a perspective view of a portion of a plating system.

FIG. 3A illustrates a perspective view of a portion of the plating system 100. FIG. 3B illustrates a perspective view of a portion of the plating system 100. The plating system 100 of FIGS. 3A and 3B can be consistent with FIGS. 1A-2 above; FIGS. 3A and 3B show additional components and steps of using the plating system 100. For example, FIG. 3 shows that the plating system 100 can include a plate 136 securable to a bottom portion of the cartridge 114. As discussed in further detail below, the lock 118 can be operated to secure the plate 136 to the bottom portion of the cartridge 114. FIG. 3 also shows that the plating system 100 can include a placement tool 138.

The placement tool 138 can include a handle 140 (shown in FIG. 4) and a shaft 142 connected thereto. The placement tool 138 can include a connector 144 connected to a distal portion of the shaft 142, as shown in FIG. 3A. The connector 144 can be insertable into the placement bore 120 of the cartridge 114 to secure the placement tool 138 to the cartridge 114, such as to allow a user to manipulate or place the cartridge 114 and the body 116 during a procedure. The plate 136 can be secured to the cartridge 114 before or after the placement tool 138 is secured to the cartridge 114.

Figure 4B:
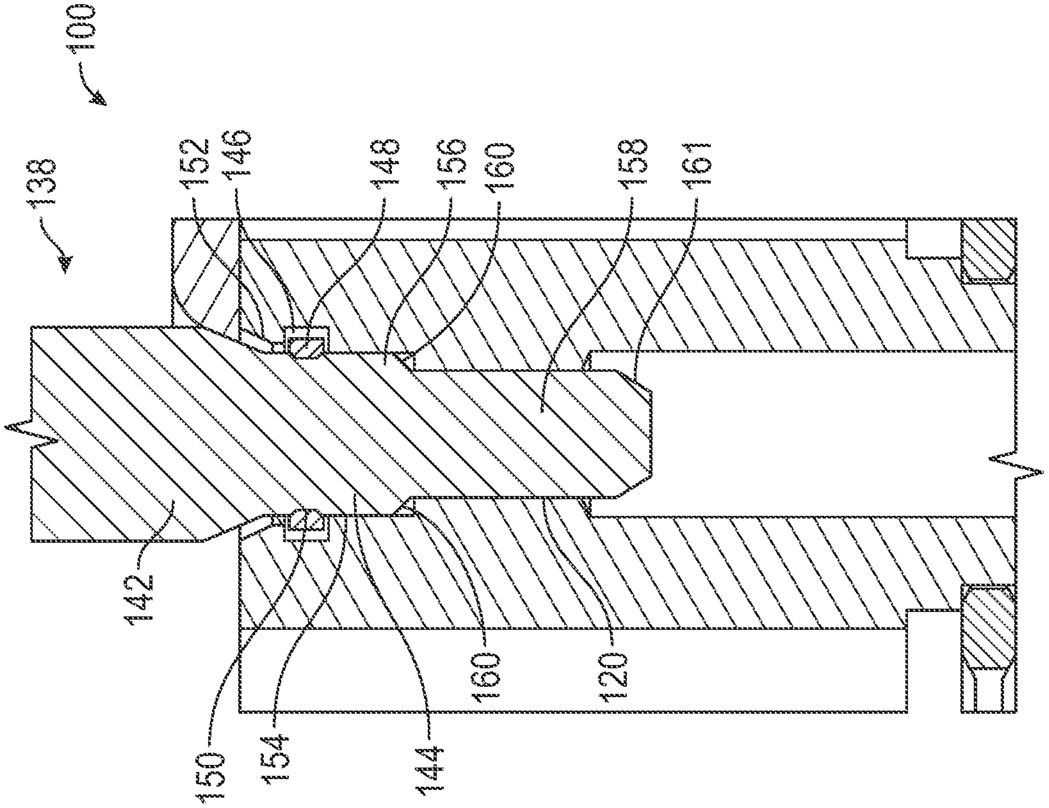
FIG. 4B illustrates a cross-sectional view of a portion of a plating system.
Figure 4A:
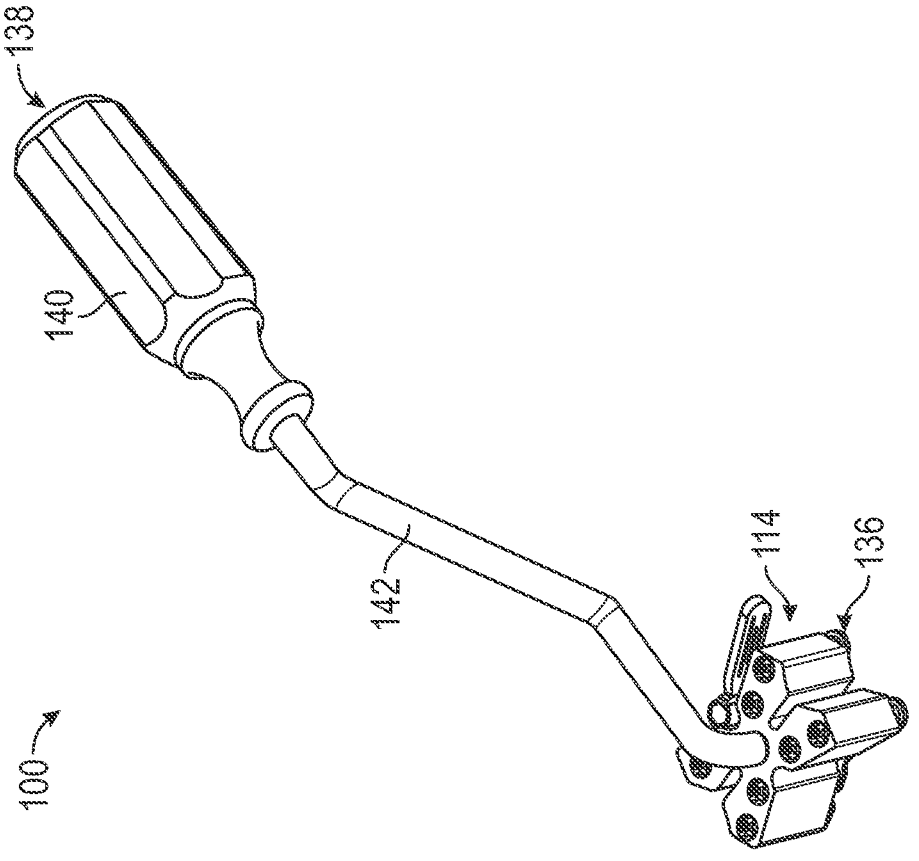
FIG. 4A illustrates a perspective view of a portion of a plating system.

FIG. 4A illustrates a perspective view of the plating system 100. FIG. 4B illustrates a cross-sectional view of the cartridge 114 and the connector 144 of the placement tool 138 of the plating system 100. FIGS. 4A and 4B are discussed together below. The plating system 100 can be consistent with the plating system 100 discussed above; FIGS. 4A and 4B show additional details of the cartridge 114 and the placement tool 138. For example, FIG. 4A shows that the placement tool 138 can include the shaft 142, which can be connected to the handle 140 at a proximal portion of the shaft 142 and can be connectable to the cartridge 114 at a distal portion of the shaft 142 (e.g., via the connector 144).

FIG. 4B shows that the connector 144 can be insertable into the placement bore 120 of the cartridge 114 such as to secure the placement tool 138 to the cartridge 114. FIG. 4B also shows that the cartridge 114 can define an undercut 146 in the placement bore 120. The undercut 146 can extend radially outward from the placement bore 120 and can be configured to retain a snap ring 148 therein. The snap ring 148 of the cartridge 114 can be insertable into a recess 150 of the connector 144 such as to securably connect the connector 144, and therefore the placement tool 138, to the cartridge 114.

FIG. 4B further shows that the placement bore 120 can include a chamfer 152 at an inlet of the placement bore 120 and can be a counterbore including a major portion 154. The connector 144 can include a stop 156 and an insertion portion 158 connected by a chamfer 160. The insertion portion 158 can include a chamfer 161 located at a distal portion of the connector 144.

The chamfers 161 and 160 of the distal tip and the stop 154, respectively, can be configured to engage the chamfer 152 of the inlet of the placement bore 120 to guide insertion of the connector 144 into the placement bore 120. The stop 154 of the connector 144 can be configured to engage the counterbore to limit insertion of the connector 144 into the placement bore 120. The chamfers 160 and 161 of the connector 144 can also help the connector 144 to pass through the snap ring 148, which can also be chamfered on both a proximal side and a distal side.

Figure 5A:
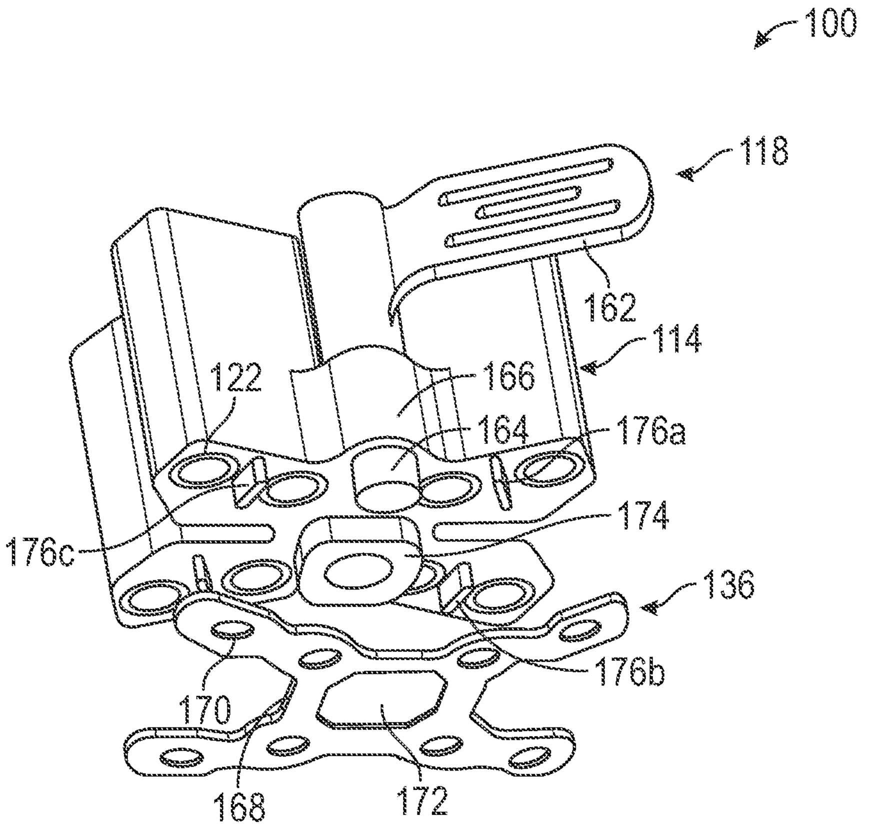
FIG. 5A illustrates a perspective view of a portion of a plating system.
Figure 5B:
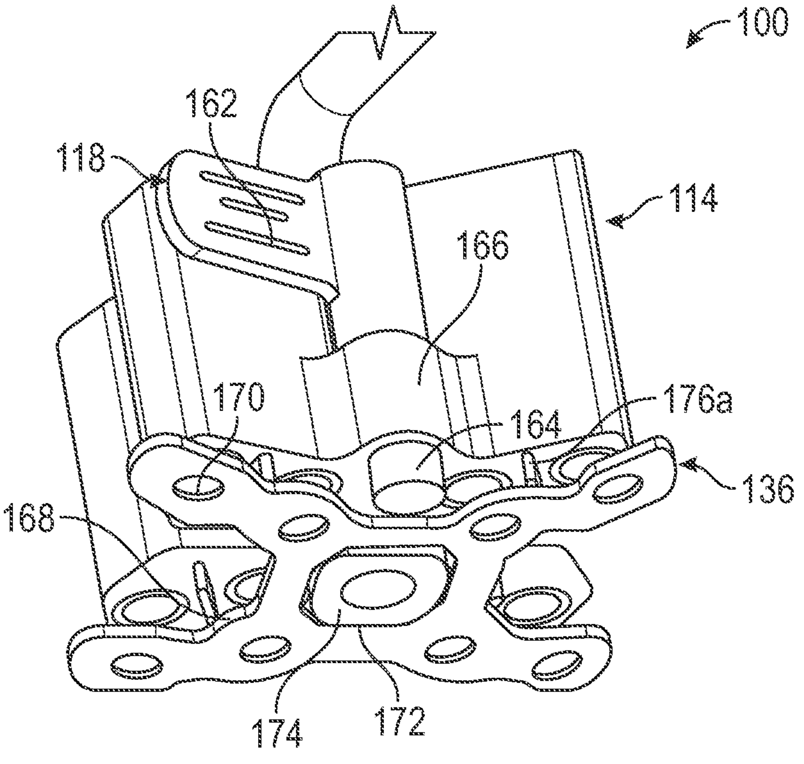
FIG. 5B illustrates a perspective view of a portion of a plating system.

FIG. 5A illustrates a perspective view of the of the cartridge 114 and the plate 136 of the plating system 100 in an unsecured position and FIG. 5B illustrates a perspective view of the of the cartridge 114 and the plate 136 of the plating system 100 in a secured position. FIGS. 5A and 5B are discussed together below. The plating system 100 can be consistent with the plating system 100 discussed above; FIGS. 5A and 5B show additional details and operation of the cartridge 114 and the plate 136.

For example, FIGS. 5A and 5B show that the lock 118 can include a handle 162 and a cam 164 secured to the handle 162. The handle 162 can be located with respect to the cartridge 114 such that the handle 162 does not interfere with a view of (or access to) the fasteners 112 within the cartridge 114. FIGS. 5A and 5B also show that the lock 118 can be secured to an outer portion or surface of the cartridge 114 via a retainer 166. Optionally, the lock 118 can be secured to other portions of the cartridge 114. FIGS. 5A and 5B also show that the handle 118 can be operated (e.g., rotated) to rotate the cam 166 with respect to the cartridge 114.

FIGS. 5A and 5B also show the plate 136 in further detail. The plate 136 can be made of materials such as metals, plastics, foams, elastomers, ceramics, composites, or combinations thereof. In some examples, the plate 136 can be comprised of biocompatible materials such as such as one or more of stainless steels, cobalt-chromium, titanium variations, polyether ether ketone (PEEK), polyether ketone ketone (PEKK), or the like. The plate 136 can include a body 168 defining a plurality of fastener bores 170 and a connection bore 172. The fasteners bores 122 can each extend through the body 168 and can be configured to receive a fastener 112 therein to secure the plate 136 to bone. The connection bore 172 can extend through the body 168 and can be configured to receive a portion of the cartridge 114 to help secure the plate 136 to the 114, as discussed in further detail below. The connection bore 172 can be optionally centered in the body 168 of the plate 136.

FIGS. 5A and 5B also show that the cartridge 114 can include a boss 174 extending from a bottom or distal portion of the cartridge 114. The boss 174 can be insertable into the connection bore 172 of the plate 136 to connect the cartridge 114 to the plate 136. The boss 174 can also help to align the retention bores 122 of the cartridge 114 with the fastener bores 170 of the plate 136 to help ensure the fasteners 112 are driven through the fastener bores 170 and into bone when the fasteners 112 are driven out of the retention bores 122 of the cartridge 114.

FIGS. 5A and 5B also show that the cartridge 114 can include projections 176*a*-176*d*, which can extend from a bottom or distal portion of the cartridge 114. The projections 176 can be configured to engage the plate 136 when the plate 136 is connected to the cartridge 114. Such engagement can help to limit movement of the plate 136 (such as rocking) with respect to the cartridge 114 when the plate 136 is secured to the cartridge 114, which can help to limit accidental disconnection of the plate 136 from the cartridge 114 when the plate 136 is secured to the cartridge 114. The projections 176 can also help to space the plate 136 away from the cartridge 114 when the plate 136 is connected to the cartridge 114 to allow the plate 136 to be bent to conform to an outer surface of a bone.

In operation, as shown in FIGS. 5A and 5B, the 136 can be positioned with respect to the cartridge 114 such that the boss 174 can be inserted into the connection bore 172 of the plate 136 to align the retention bores 122 with the fastener bores 170. Once the boss 174 is secured to the plate 136, the handle 162 of the lock 118 can be operated to rotate the cam 164 with respect to the cartridge 114 and the plate 136 and to engage the body 168 of the plate 136 to secure the plate 136 to the cartridge 114.

Figure 6:
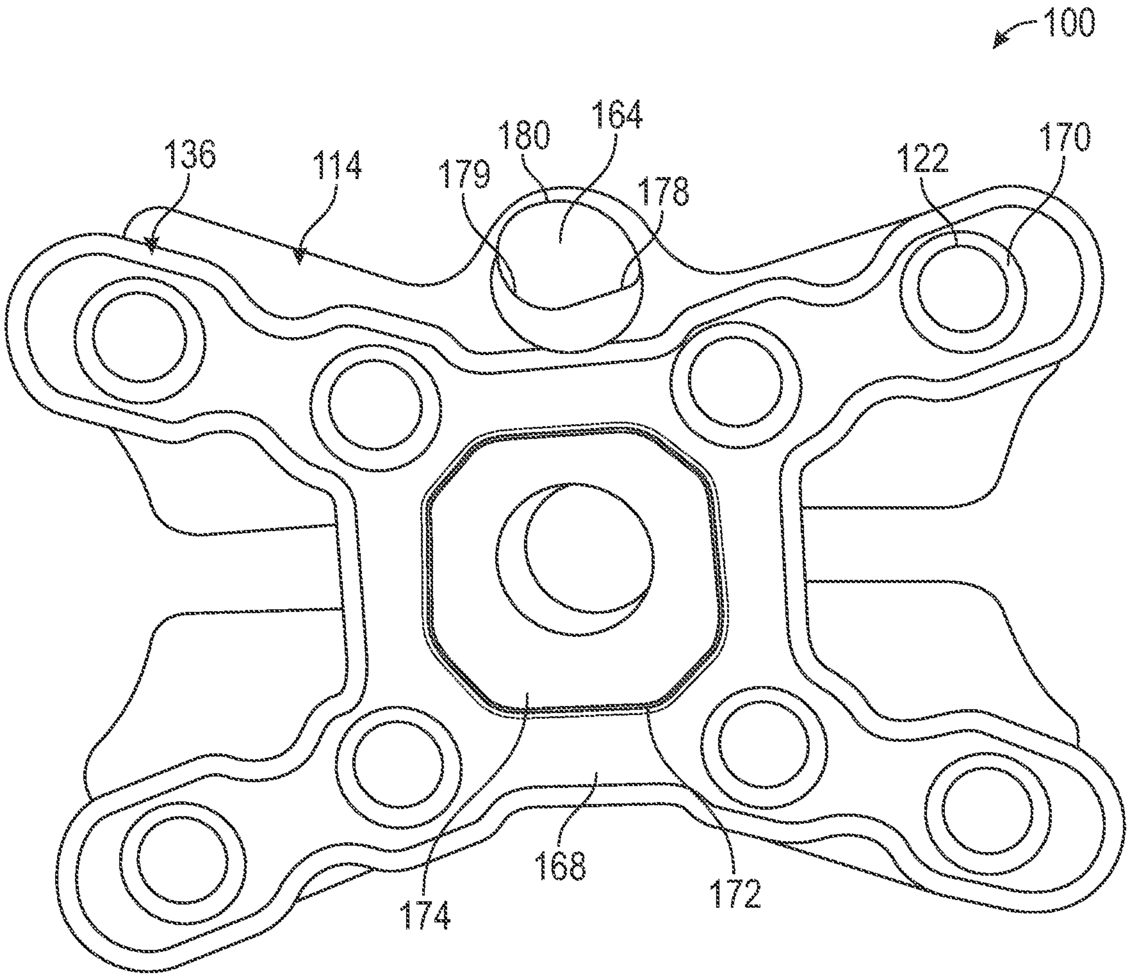
FIG. 6 illustrates a bottom view of a portion of a plating system.

FIG. 6 illustrates a bottom view of the plate 136 and the cartridge 114 of the plating system 100. The plating system 100 can be consistent with the plating system 100 discussed above; FIG. 6 shows additional details and operation of the cartridge 114 and the plate 136. For example, FIG. 6 shows how when the boss 174 is positioned in the connection bore 172, the fastener bores 170 align with the retention bores 122

FIG. 6 also shows that when the handle 162 is in the unlocked position, a recess 178 of the cam 164 can be positioned near the body 168 of the plate 136 such that the cam 164 is unlocked from the plate 136. Then, when the handle 162 is rotated to the locked position, a locking surface 180 can be rotated to engage the body 168 to secure the body 168 between the cam 164 and the boss 174 in a friction fit, clamping, or interference arrangement. A ramped surface 179 can connect the recess 178 to the locking surface

180 to provide a gradual engagement between the locking surface 180 and the body 168 during locking of the cam 164 to the body 168. When it is desired to separate the plate 136 from the cartridge 114, the cam 164 can be rotated such that the recess 178 is positioned near the body 168 and the plate 136 can be separated from the boss 174 and the cartridge 114.

Figure 7A:
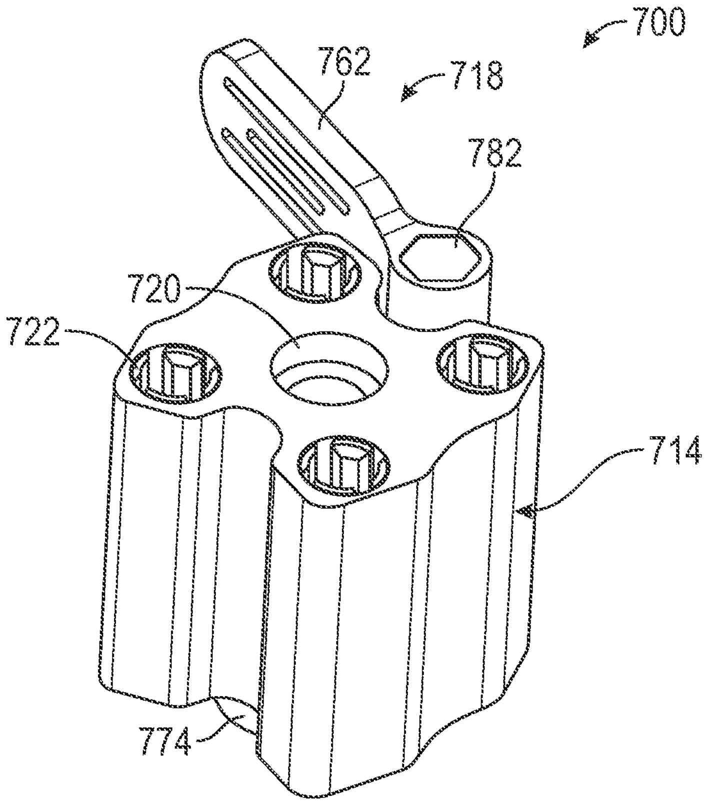
FIG. 7A illustrates a perspective view of a portion of a plating system.
Figure 7B:
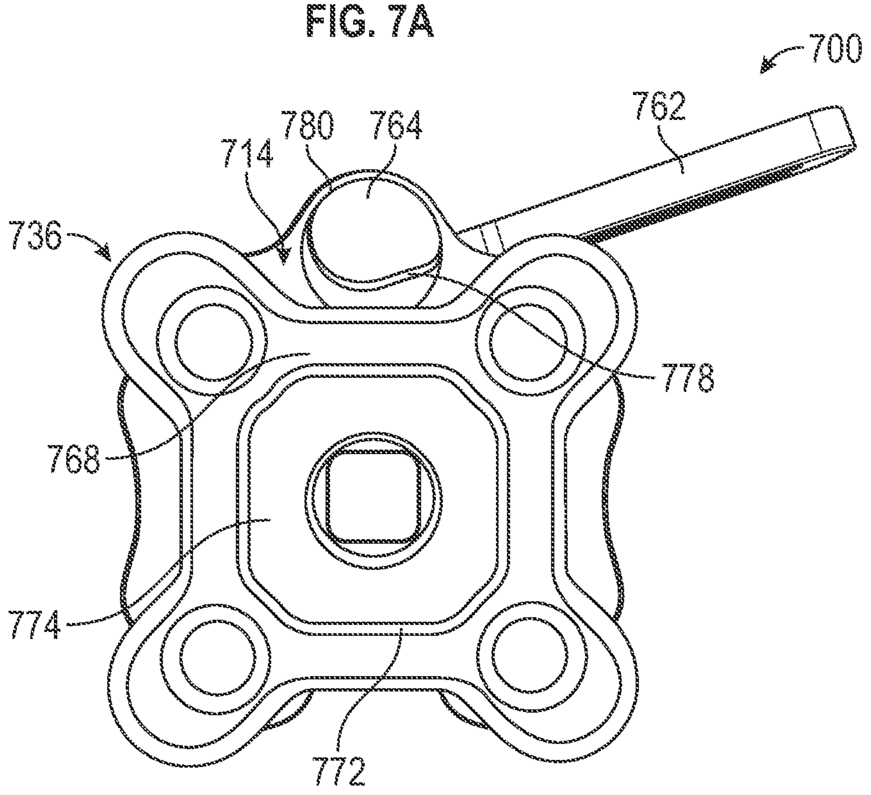
FIG. 7B illustrates a bottom view of a portion of a plating system.

FIG. 7A illustrates a perspective view of a portion of a plating system 700. FIG. 7B illustrates a bottom view of a portion of the plating system 700. The plating system 700 can be similar to the plating system 100 discussed above; the plating system 700 can differ in that it can include a cartridge and a plate having a square bore pattern. Any of the plating systems discussed above or below can be modified to include such a pattern. FIG. 7A also shows that a lock 718 can include a shaft 782 connected to a cam 764 and a handle 762. The shaft 782 can have a hexagonal shape (or can have a square or other shape in other examples) to help limit relative rotation of the handle 762 and the cam 764

Figure 8A:
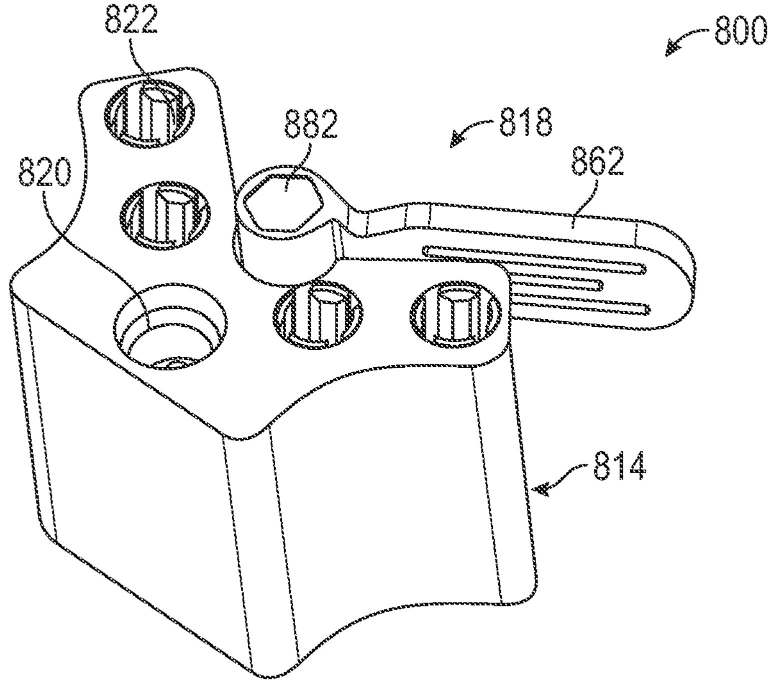
FIG. 8A illustrates a perspective view of a portion of a plating system.
Figure 8B:
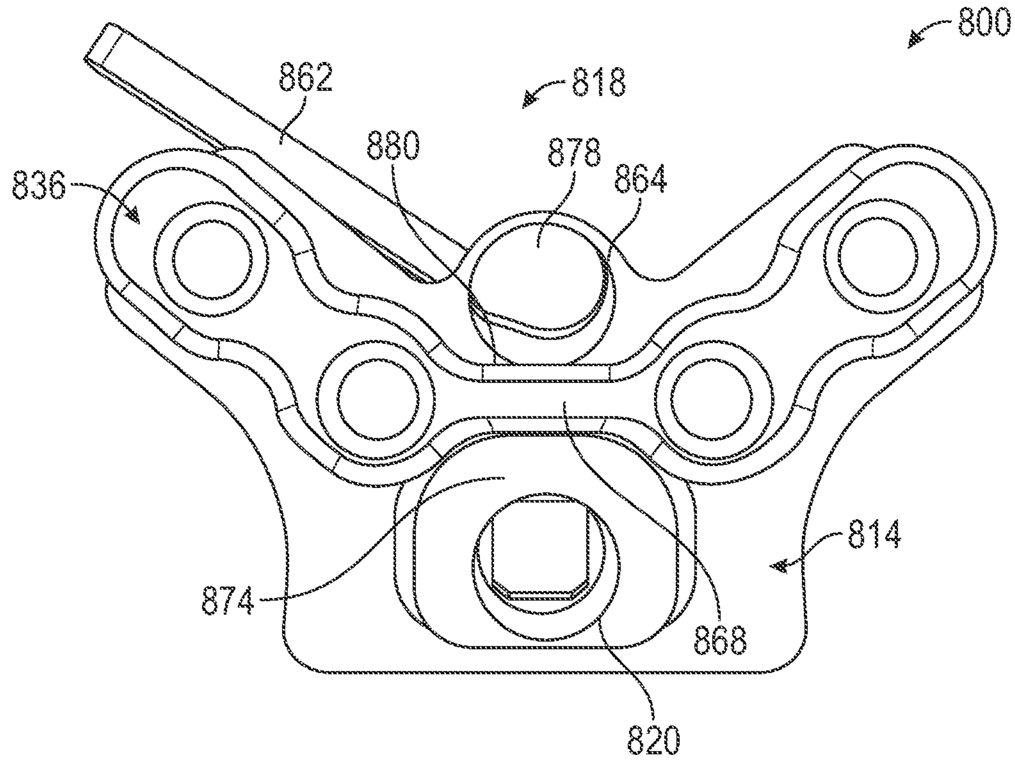
FIG. 8B illustrates a bottom view of a portion of a plating system.

FIG. 8A illustrates a perspective view of a portion of a plating system 800. FIG. 8B illustrates a bottom view of a portion of the plating system 800. The plating system 800 can be similar to the plating system 800 discussed above; the plating system 800 can differ in that it can include a cartridge and a plate having an L-shape or L-shape bore pattern. Any of the plating systems discussed above or below can be modified to include such a pattern. FIG. 8B also shows how a boss 874 can engage a first side of a body 868 of a plate 836 and how a locking surface 880 of a cam 864 can engage the opposite side of the body 868 when a handle 862 of a lock 818 is moved to the locked position. FIG. 8B also shows that the boss 874 can be shaped to conform to the body 868 of the plate 836 to improve engagement between a cartridge 814 and the plate 836.

Figure 9:
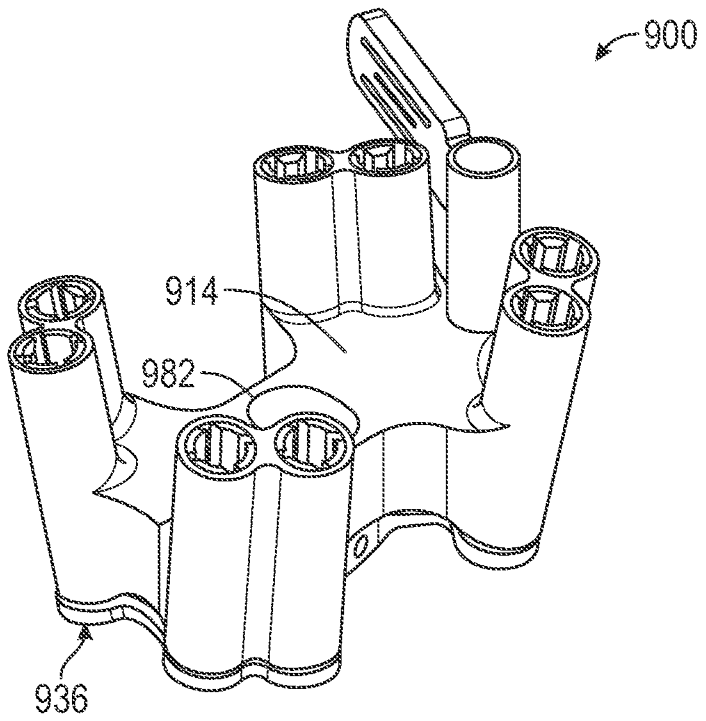
FIG. 9 illustrates a perspective view of a portion of a plating system.

FIG. 9 illustrates a perspective view of a portion of a plating system 900. The plating system 900 can be similar to the plating system 900 discussed above; the plating system 900 can differ in that it can include a cartridge 914 having perimeter bores such as to accommodate a cerclage connected to the plate 936. Any of the plating systems discussed above or below can be modified to include such features. The cartridge 914 can also include a connection bore 982 including a viewing window to view the cerclage connected to the plate 936. Optionally, the cartridge 914 can be configured to accommodate flat plates, contourable plates, or pre-contoured plates.

Figure 10:
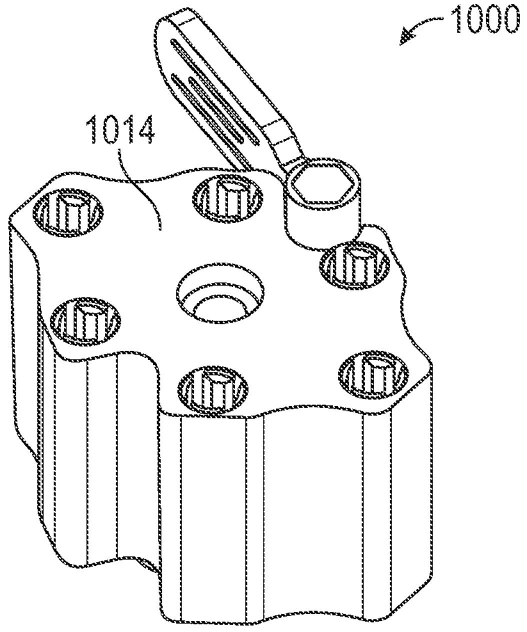
FIG. 10 illustrates a perspective view of a portion of a plating system.

FIG. 10 illustrates a perspective view of a portion of a plating system 1000. The plating system 1000 can be similar to the plating system 1000 discussed above; the plating system 1000 can differ in that it can include a cartridge 1014 and a plate having perimeter bores. Any of the plating systems discussed above or below can be modified to include such a pattern.

Figure 11:
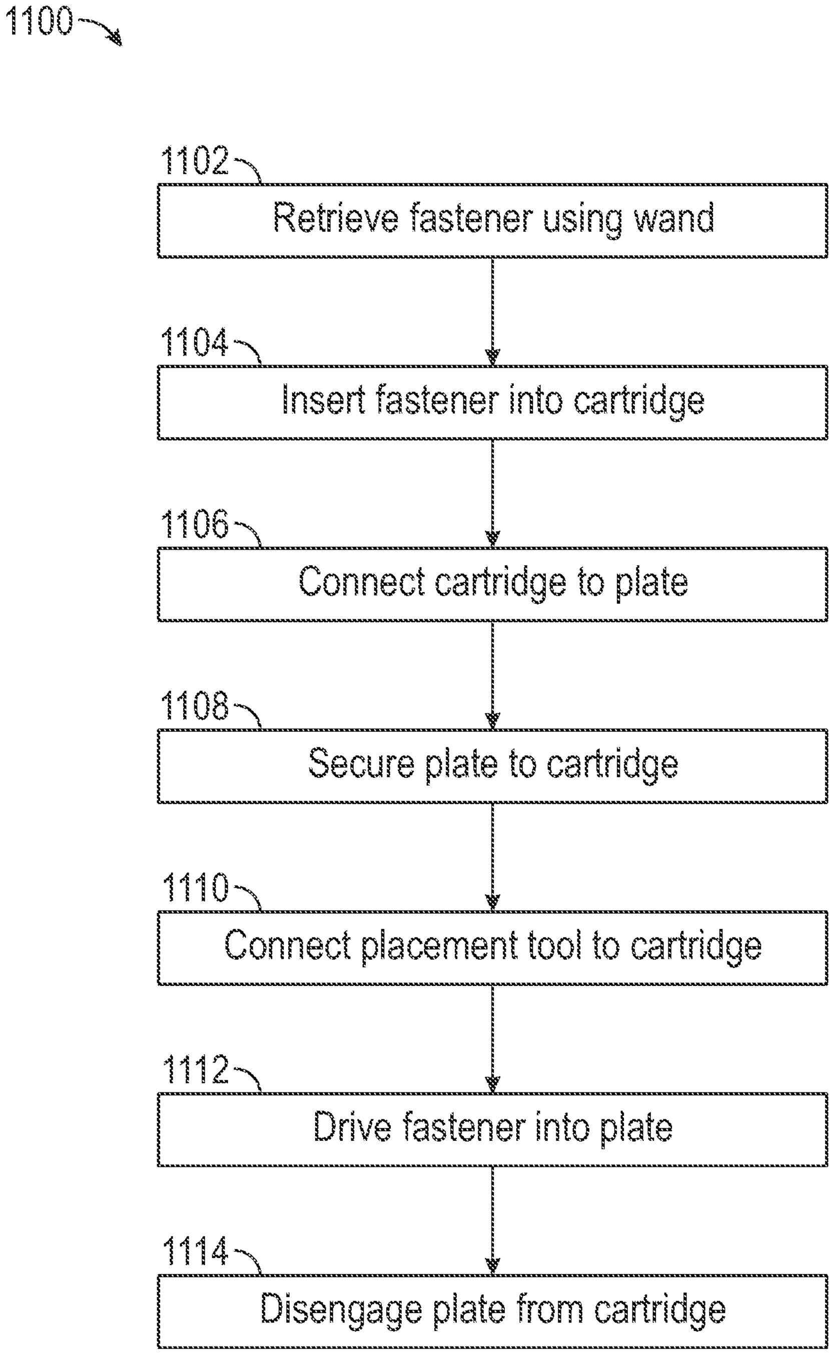
FIG. 11 illustrates a schematic view of a method.

FIG. 11 illustrates a schematic view of a method 1100, in accordance with at least one example of this disclosure. The method 1100 can be a method of repairing a sternotomy using a plating system. More specific examples of the method 1100 are discussed above and below. The steps or operations of the method 1100 are illustrated in a particular order for convenience and clarity; many of the discussed operations can be performed in a different sequence or in parallel without materially impacting other operations. The method 1100 as discussed includes operations performed by multiple different actors, devices, and/or systems. It is understood that subsets of the operations discussed in the method 1100 can be attributable to a single actor, device, or system could be considered a separate standalone process or method.

Prior to the steps of the method 1100 being performed, a sternotomy or midline resection can be created in a sternum. When it is desired to close the sternum, a step 1102 can be performed where a user can operate a wand to retrieve a fastener. For example, a user can operate a wand 102 to retrieve a fastener 112. At step 1104, a first retention feature of the retention bore can be engaged with the fastener to deflect the first retention feature to engage a second retention feature with the fastener to retain the fastener within the retention bore to insert the fastener into a retention bore of a cartridge using the wand. For example, the first retention feature 130*a* of the retention bore 122*a* can be engaged with the fastener 112*a* to deflect the first retention feature 130*a* to engage a second retention feature 132*a* with the fastener to retain the fastener 112*a* within the retention bore 122*a* to insert the fastener 112*a* into the retention bore 120*a* of the cartridge 114 using the wand 102.

At step 1106, a boss of the cartridge can be inserted into a connection bore of a plate to align the retention bore with a fastener bore of the plate. For example. For example, the boss 174 of the cartridge 114 can be inserted into a connection bore 172 of a plate 136 to align the retention bores 122 with the fastener bores 122 of the plate 136.

At step 1108, a cam of the cartridge can be operated to engage a body of the plate to secure the plate to the cartridge. For example, the cam 164 of the cartridge 114 can be operated to engage the body 168 of the plate 136 to secure the plate 136 to the cartridge 114. At step 1110, a placement tool can be connected to a cartridge. For example, the placement tool 138 can be connected to the cartridge 114. At step 1112, a fastener can be driven from the cartridge into the plate and into bone. For example, the fastener 112*a* can be driven from the cartridge 114 (e.g., out of the retention bore 122*a*) into one of the fastener bores 170 of plate 136 and into bone. At step 1114, the plate can be disengaged or disconnected from the cartridge. For example, the lock 118 can be operated to disengage the cam 164 from the plate 136 to disconnect the plate 136 from the cartridge 114.

Though above devices and methods are discussed herein with reference to a sternum or sternotomy, the devices and methods can be used with other bones or bone portions. For example, the plate 136 and the cartridge 114 can be configured and used to repair a fractured rib, clavicle, femur, tibia, fibula, humerus, radius, ulna, or the like.

NOTES AND EXAMPLES

The following, non-limiting examples, detail certain aspects of the present subject matter to solve the challenges and provide the benefits discussed herein, among others.

Example 1 is a plate system for securing to a bone, the plate system comprising: a plate including a plate body, the plate body defining: a fastener bore configured to receive a fastener for securing the plate to the bone; and a connection bore; a cartridge including a cartridge body, the cartridge body defining: a retention bore configured to retain a fastener therein; and a boss insertable into the connection bore to align the retention bore with the fastener bore; and an actuator connected to the cartridge and operable to secure the plate to the cartridge.

In Example 2, the subject matter of Example 1 optionally includes wherein the actuator includes a cam rotatable between a locked position and an unlocked position, the cam engageable with the plate body in the locked position to secure the plate to the cartridge.

In Example 3, the subject matter of Example 2 optionally includes wherein the actuator includes a handle operable to rotate the cam.

In Example 4, the subject matter of any one or more of Examples 1-3 optionally include wherein the cartridge body includes a retention feature extending into the retention bore to retain the fastener within the retention bore.

In Example 5, the subject matter of Example 4 optionally includes wherein the retention feature is configured to reversibly deflect outward to allow the fastener to pass through the retention bore of the cartridge and into the fastener bore of the plate.

In Example 6, the subject matter of Example 5 optionally includes wherein the retention feature at least partially defines the retention bore.

In Example 7, the subject matter of any one or more of Examples 1-6 optionally include wherein the cartridge body includes a plurality of projections extending from the body to engage the plate when the boss is inserted into the connection bore.

In Example 8, the subject matter of any one or more of Examples 1-7 optionally include wherein the plate body defines a plurality of fastener bores and wherein the cartridge body includes a plurality of retention bores, each retention bore alignable with one of the plurality of fastener bores when the boss is inserted into the connection bore.

In Example 9, the subject matter of any one or more of Examples 1-8 optionally include a placement tool including: a handle; a shaft including a proximal portion extending from the handle and a distal portion opposite the proximal portion; and a connector connected to the distal portion of the shaft.

In Example 10, the subject matter of Example 9 optionally includes wherein the cartridge body includes a placement bore configured to receive the connector therein to secure the placement tool to the cartridge body.

In Example 11, the subject matter of Example 10 optionally includes wherein the cartridge body includes a snap connector located at least partially within the placement bore and configured to engage the connector to secure the placement tool to the cartridge body.

Example 12 is a fastener cartridge comprising: a body defining a plurality of retention bores each extending through the body and each configured to retain a fastener therein; a boss extending from the body and insertable into a connection bore of a bone plate to align each retention bore with a fastener bore of the bone plate; a cam connected to the body and rotatable between a locked position and an unlocked position, the cam engageable with a body of the plate in the locked position to secure the plate to the cartridge; and an actuator connected to the cartridge and operable to rotate the cam.

In Example 13, the subject matter of Example 12 optionally includes wherein the body includes a retention feature extending into the retention bore to retain the fastener within the retention bore.

In Example 14, the subject matter of Example 13 optionally includes wherein the retention feature is configured to reversibly deflect outward to allow the fastener to pass through the retention bore and into a fastener bore of the plate.

In Example 15, the subject matter of Example 14 optionally includes wherein the retention feature at least partially defines the retention bore.

In Example 16, the subject matter of any one or more of Examples 12-15 optionally include wherein the body includes a plurality of projections extending from the body to engage the plate when the boss is inserted into the connection bore.

Example 17 is a method for using a fastener cartridge, the method comprising: operating a wand to retrieve a fastener; inserting the fastener into a retention bore of a cartridge using the wand; inserting a boss of the cartridge into a connection bore of a plate to align the retention bore with a fastener bore of the plate; and operating a cam of the cartridge to engage a body of the plate to secure the plate to the cartridge.

In Example 18, the subject matter of Example 17 optionally includes wherein inserting the fastener into the retention bore includes engaging a first retention feature of the retention bore with the fastener to deflect the first retention feature to engage a second retention feature with the fastener to retain the fastener within the retention bore.

In Example 19, the subject matter of Example 18 optionally includes driving the fastener past the second retention feature and into the fastener bore.

In Example 20, the subject matter of Example 19 optionally includes wherein driving the fastener past the second retention feature includes reversibly deflecting the second retention feature.

In Example 21, the subject matter of any one or more of Examples 19-20 optionally include securing the fastener to bone.

In Example 22, the subject matter of Example 21 optionally includes operating the cam of the cartridge to disengage the body of the plate.

In Example 23, the apparatuses or method of any one or any combination of Examples 1-22 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A plate system for securing to a bone, the plate system comprising:
- a plate including a plate body, the plate body defining:
  - a fastener bore configured to receive a fastener for securing the plate to the bone; and
  - a connection bore;
- a cartridge including a cartridge body, the cartridge body defining:
  - a retention bore configured to retain a fastener therein; and
  - a boss insertable into the connection bore to align the retention bore with the fastener bore; and
- an actuator connected to the cartridge and operable to secure the plate to the cartridge, the actuator including a cam rotatable between a locked position and an unlocked position, and the cam engageable with the plate body in the locked position to secure the plate to the cartridge.

2. The plate system of claim 1, wherein the actuator includes a handle operable to rotate the cam.

3. The plate system of claim 1, wherein the cartridge body includes a retention feature extending into the retention bore to retain the fastener within the retention bore.

4. The plate system of claim 3, wherein the retention feature is configured to reversibly deflect outward to allow the fastener to pass through the retention bore of the cartridge and into the fastener bore of the plate.

5. The plate system of claim 4, wherein the retention feature at least partially defines the retention bore.

6. The plate system of claim 1, wherein the cartridge body includes a plurality of projections extending from the plate body to engage the plate when the boss is inserted into the connection bore.

7. The plate system of claim 1, wherein the plate body defines a plurality of fastener bores and wherein the cartridge body includes a plurality of retention bores, each retention bore alignable with one of the plurality of fastener bores when the boss is inserted into the connection bore.

8. The plate system of claim 1, further comprising:
- a placement tool including:
  - a handle;
  - a shaft including a proximal portion extending from the handle and a distal portion opposite the proximal portion; and
  - a connector connected to the distal portion of the shaft.

9. The plate system of claim 8, wherein the cartridge body includes a placement bore configured to receive the connector therein to secure the placement tool to the cartridge body.

10. The plate system of claim 9, wherein the cartridge body includes a snap connector located at least partially within the placement bore and configured to engage the connector to secure the placement tool to the cartridge body.

11. A fastener cartridge comprising:
- a body defining a plurality of retention bores each extending through the body and each configured to retain a fastener therein;
- a boss extending from the body and insertable into a connection bore of a bone plate to align each retention bore with a fastener bore of the bone plate;
- a cam connected to the body and rotatable between a locked position and an unlocked position, the cam engageable with a body of the bone plate in the locked position to secure the bone plate to the fastener cartridge; and
- an actuator connected to the fastener cartridge and operable to rotate the cam.

12. The fastener cartridge of claim 11, wherein the body includes a retention feature extending into a retention bore of the plurality of retention bores to retain the fastener within the retention bore.

13. The fastener cartridge of claim 12, wherein the retention feature is configured to reversibly deflect outward to allow the fastener to pass through the retention bore and into a fastener bore of the bone plate.

14. The fastener cartridge of claim 13, wherein the retention feature at least partially defines the retention bore.

15. The fastener cartridge of claim 11, wherein the body includes a plurality of projections extending from the body to engage the bone plate when the boss is inserted into the connection bore.

16. A method for using a fastener cartridge, the method comprising:
- operating a wand to retrieve a fastener;
- inserting the fastener into a retention bore of a cartridge using the wand;
- inserting a boss of the cartridge into a connection bore of a plate to align the retention bore with a fastener bore of the plate; and
- operating a cam of the cartridge to engage a body of the plate to secure the plate to the cartridge.

17. The method of claim 16, wherein inserting the fastener into the retention bore includes engaging a first retention feature of the retention bore with the fastener to deflect the first retention feature to engage a second retention feature with the fastener to retain the fastener within the retention bore.

18. The method of claim 17, further comprising:
- driving the fastener past the second retention feature and into the fastener bore.

19. The method of claim 18, wherein driving the fastener past the second retention feature includes reversibly deflecting the second retention feature.

* * * * *